United States Patent
Kakuta et al.

(10) Patent No.: US 8,802,449 B2
(45) Date of Patent: Aug. 12, 2014

(54) MICROCHIPS, KITS, AND METHODS FOR IMMUNOASSAYS

(75) Inventors: Masaya Kakuta, Kanagawa (JP);
Manabu Tokeshi, Kanagawa (JP);
Hitoshi Izumida, Kanagawa (JP);
Takahide Takadera, Kanagawa (JP);
Kenji Miyagawa, Kanagawa (JP)

(73) Assignees: Institute of Microchemical Technology, Kanagawa (JP); Kansai Paint Co., Ltd., Hyogo (JP)

( * ) Notice: Subject to any disclaimer, the term of this patent is extended or adjusted under 35 U.S.C. 154(b) by 1399 days.

(21) Appl. No.: 12/159,371

(22) PCT Filed: Dec. 25, 2006

(86) PCT No.: PCT/JP2006/325730
§ 371 (c)(1),
(2), (4) Date: Feb. 27, 2009

(87) PCT Pub. No.: WO2007/074756
PCT Pub. Date: Jul. 5, 2007

(65) Prior Publication Data
US 2010/0261205 A1    Oct. 14, 2010

(30) Foreign Application Priority Data
Dec. 26, 2005  (JP) ................................. 2005-372921

(51) Int. Cl.
*G01N 33/544* (2006.01)

(52) U.S. Cl.
USPC ........... 436/535; 436/518; 436/524; 436/541; 436/177; 435/7.1; 435/283.1; 435/287.1; 435/287.2; 435/288.7; 435/288.5

(58) Field of Classification Search
USPC ........... 436/518, 524, 535, 541, 177; 435/7.1, 435/283.1, 287.1, 287.2, 288.7, 288.5
See application file for complete search history.

(56) References Cited

U.S. PATENT DOCUMENTS

| 5,990,191 A | 11/1999 | Kikuta et al. |
| 6,156,270 A * | 12/2000 | Buechler ...................... 422/417 |

(Continued)

FOREIGN PATENT DOCUMENTS

| JP | 2005-69997 A | 3/2005 |
| WO | WO 97/19978 A1 | 6/1997 |
| WO | WO 03/062823 A1 | 7/2003 |
| WO | WO 2004/083823 A | 9/2004 |

OTHER PUBLICATIONS

Jeong et al; "Continuous Fabrication of Biocatalyst Immobilized Microparticles Using Photopolymerization and Immiscible Liquids in Microfluidic Systems", Langmuir, 2005, 21, pp. 3738-3741.

(Continued)

*Primary Examiner* — Melanie Y Brown
(74) *Attorney, Agent, or Firm* — Arent Fox LLP

(57) ABSTRACT

An objective of the present invention is to provide immunoassay microchips in which microstructures of beads having a sufficient reaction area were constructed within microchannels while suppressing flow path resistance, and to provide simple and highly-sensitive immunoassay methods for microsamples. The objective was achieved by immunoassay microchips comprising microchannels with microstructures arranged in at least a portion of the microchannels, the microstructures retaining microbeads uniformly dispersed in photo-cured hydrophilic resins, and the microbeads having a primary antibody immobilized on their surfaces, and by immunoassay methods using the microchips.

7 Claims, 11 Drawing Sheets

(56) References Cited

U.S. PATENT DOCUMENTS

| | | | |
|---|---|---|---|
| 6,368,871 B1* | 4/2002 | Christel et al. | 436/180 |
| 6,454,924 B2* | 9/2002 | Jedrzejewski et al. | 204/601 |
| 6,685,841 B2* | 2/2004 | Lopez et al. | 210/767 |
| 7,262,063 B2* | 8/2007 | Banerjee et al. | 436/524 |
| 7,666,662 B2* | 2/2010 | Kohara et al. | 435/287.1 |
| 2003/0006143 A1* | 1/2003 | Banerjee et al. | 205/414 |
| 2003/0190608 A1* | 10/2003 | Blackburn | 435/6 |
| 2005/0142624 A1 | 6/2005 | Kitamori et al. | |
| 2005/0239195 A1* | 10/2005 | Oram et al. | 435/288.3 |
| 2006/0000772 A1* | 1/2006 | Sano et al. | 210/635 |
| 2006/0134599 A1* | 6/2006 | Toner et al. | 435/4 |
| 2006/0160162 A1* | 7/2006 | Fulwyler et al. | 435/7.92 |
| 2006/0177350 A1 | 8/2006 | Sano et al. | |

OTHER PUBLICATIONS

Maruyama et al, "Immobilization of Individual cells by local photo-polymerization on a chip", The Analyst, 2005, 130, pp. 304-310.

Delamarche, Emmanuel et al., "Microfluidics for Processing Surfaces and Miniaturizing Biological Assays"; Adv. Mater. 2005, 17, 2911-2933.

* cited by examiner

MICROCHIPS, KITS, AND METHODS FOR IMMUNOASSAYS

The present application is a National Phase of International Application No. PCT/JP2006/325730 filed Dec. 25, 2006 and claims priority to Japanese Patent Application No. 2005-372921 filed Dec. 26, 2005. The contents of both applications are expressly incorporated herein by reference in their entireties.

TECHNICAL FIELD

The present invention relates to immunoassay microchips and immunoassay methods using the microchips. Specifically, the present invention relates to immunoassay microchips and immunoassay kits comprising microstructures for immunoassays, which are formed in micro-flow paths by light-exposure treatment of hydrophilic photo-curable resin solutions in which microbeads are uniformly dispersed. The present invention also relates to immunoassay methods using the microchips.

BACKGROUND ART

Patent Document 1 describes enzyme immunoassay chips and enzyme immunoassay methods, in which beads carrying an antibody immobilized on their surface are introduced into microchannels formed on a substrate and the introduced beads are trapped by a trapping portion, which is then used as an immunoassay column. Enzymatic reaction products flowing over the trapping portion are analyzed with an analyzer unit such as a thermal lens microscope.

This enables a great reduction of the analyte amount as well as the time required for detection since manipulations are simple, as compared to immunoassays using conventional microtiter plates.

Meanwhile, microorganism-immobilizing particulate carriers with surfaces suitable for adhesion of microorganisms are known (Patent Document 2). These carriers are prepared by adding dropwise a liquid composition to an aqueous medium containing an alkaline metal or a polyvalent metal ion to allow gelation of the composition into granular form, and then curing the granules by irradiation with active rays. The liquid composition contains a hydrophilic curable resin, a photopolymerization initiator, and a water-soluble polymer polysaccharide capable of gelation upon contact with the alkaline metal or polyvalent metal ion.

Also known is a technology for immobilizing a single cell within a microchip, where photopolymerization for single-cell-level experiments is applied. In this technology, photo-crosslinkable resin droplets are dispersed in a cell-containing solution within a microchannel; a desired cell is selected using a microscope; a laser is irradiated around the cell to locally photopolymerize the surrounding photo-crosslinkable resin; and only the selected cell is immobilized on the microchip. The relationship between irradiation time and diameter of curable resin is also known (see Non-Patent Document 1).

[Patent Document 1]
International Patent Application Publication No. WO 2003/062823

[Patent Document 2]
International Patent Application Publication No. WO 97/19978

[Non-Patent Document 1]
Maruyama, H., and three other authors, "Immobilisation of individual cells by local photo-polymerisation on a chip", "The Analyst", The Royal Society of Chemistry, 130, p. 304-310 (Jan. 31, 2005)

DISCLOSURE OF THE INVENTION

Problems to be Solved by the Invention

The analyte amount could be greatly reduced by using microchannels as described in Patent Document 1. However, the reaction product amount was also greatly decreased due to the reduced analyte amount. As a result, special analytical devices such as thermal lens microscopes were required to analyze the products. This naturally limited circumstances where this analysis could be applied.

An approach for solving these technical problems is to improve reaction efficiency, thereby producing a sufficient amount of reaction products even when the analyte amount is low. To improve reaction efficiency, the reaction area needs to be increased, and thus further reduction of bead diameter is essential.

When the bead diameter is further reduced, however, manipulation of beads (for example, introducing beads into a trap to construct a column) naturally becomes more difficult. In addition, when a liquid such as an analyte is loaded into a microchannel filled with many such small-diametered beads it is expected that the treated liquid would fail to flow through the microchannel since flow path resistance is very high, as apparent from the space between the beads.

Meanwhile, technologies for immobilizing microorganisms or cells separately on bead-shaped hydrophilic photo-curable resins are known from Patent Document 2 and Non-patent Document 1. However, nothing teaches preparing columns in microchannels by forming a reaction phase with antibody-immobilized microbeads while keeping flow path resistance low.

Means for Solving the Problems

Hence, the present inventors explored techniques for constructing microbead columns in which the flow path resistance is suppressed within a practically permissible range. As a result, the present inventors devised a technique for suppressing flow path resistance by dividing the cross-section of a microchannel into a flow path portion and a column portion retaining uniformly-dispersed beads.

However, when the hydrophilicity of the column portion retaining uniformly-dispersed beads is low, the function as a column is almost completely lost even if a liquid such as an analyte can flow down through the microchannel. Thus, there was a need for a technique for constructing three-dimensional structures with hydrophilicity high enough to enable permeation and diffusion of liquids between the column portion and the flow path portion.

Furthermore, microchannels for immunoassays carry the following problems: it is difficult keep desired columns or such prepared before flow path formation, since high temperature treatment or the like cannot be performed after the introduction of beads and such, to avoid denaturation of antibodies, etc; and it is also quite difficult to subsequently construct three-dimensional structures such as columns with uniformly-dispersed beads in microchannels after the formation of the microchannels.

To construct three-dimensional structures after the formation of microchannels, the present inventors initially examined the applicability of the lithography technique with light exposure treatment of photo-curable resins, which is a representative technology of three-dimensional molding. However, even if desired three-dimensional structures could be constructed in microchannels, the inventors discovered that the original function as a bead column was not achieved by simply using a conventional photo-curable resin solution.

Thus, to enable sufficient transfer of substances between the flow path portion and the bead column portion, the present inventors studied dilution ratios and light exposure conditions for photo-curable resin solutions, as well as three-dimensional structures, in a curing treatment that can retain beads loosely enough to maintain the external shape of the three-dimensional structures.

As a result, the present inventors discovered that even a photo-curable resin solution that is diluted to less than 30% of the initial concentration, and in which beads with an immobilized primary antibody are suspended, can form columnar structures with an external diameter of about 40 μm and a height of about 100 μm, which do not collapse even by centrifugation or such. The inventors also discovered that the increase in flow path resistance due to the construction of the three-dimensional structures was small since the flow path in the microchannel was secured between columns, thus resulting in hardly no interference on manipulations.

The present invention (1) is an immunoassay microchip, comprising a flow path(s) with a microstructure(s), wherein the microstructure(s) retains microbeads uniformly dispersed in a photo-cured hydrophilic resin, and the microbeads have a primary antibody immobilized on their surface.

The present invention (2) is the immunoassay microchip of the present invention (1), wherein the microstructure(s) is patterned into an arbitrary shape by light exposure treatment of the hydrophilic light-curable resin solution in which the microbeads are suspended.

The present invention (3) is the immunoassay microchip of the present invention (1), wherein the microstructure(s) is patterned by light exposure treatment of the hydrophilic light-curable resin solution in which microbeads having a primary antibody immobilized on their surface are suspended, wherein the hydrophilic light-curable resin solution has been introduced into the periphery of microstructures patterned by the light exposure treatment of the hydrophilic light-curable resin solution.

The present invention (4) is the immunoassay microchip of any one of the present inventions (1) to (3), wherein a microstructure(s) retaining uniformly dispersed microbeads that have a primary antibody immobilized on their surface and have different color tones are sequentially arranged along the flow path(s).

The present invention (5) is the immunoassay microchip of any one of the present inventions (1) to (4), wherein the flow path(s) is formed by a canal formed on a substrate and a cover plate that comprises at least an opening.

The present invention (6) is the immunoassay microchip of any one of the present inventions (1) to (5), wherein the flow path(s) is 100 μm or more and 5000 μm or less in width and 50 μm or more and 200 μm or less in depth, and wherein at least a portion of the flow path(s) comprises a region with a flow path cross-sectional area that enables a liquid introduced by a capillarity to flow down in the direction of the flow path(s).

The present invention (7) is the immunoassay microchip of any one of the present inventions (1) to (4), wherein the flow path(s) is a space compartmentalized with the inner surface of a capillary comprising at least an opening.

The present invention (8) is the immunoassay microchip of any one of the present inventions (1) to (4), wherein the flow path(s) is in a columnar shape with a diameter of 50 μm or more and 1000 μm or less, or in a prismatic shape with a side length of 50 μm or more and 1000 μm or less, and wherein the flow path(s) is a space compartmentalized with the inner surface of a capillary comprising at least an opening.

The present invention (9) is a kit for immunoassay, wherein the immunoassay microchip of any one of the present inventions (1) to (8) is packed together with a solution comprising a labeled secondary antibody or a solution comprising a labeled antigen, a washing solution, and a reagent solution comprising a substrate, such that the solutions can be introduced into a flow path of the microchip.

The present invention (10) is an immunoassay method using a test chip that comprises a flow path(s) in which a microstructure(s) is arranged, wherein the method comprises at least the steps of:

preparing a substrate comprising at least one flow path;

introducing a hydrophilic light-curable resin solution in which microbeads having a primary antibody immobilized on their surface are suspended, and filling the flow path(s) with the hydrophilic light-curable resin solution by capillary effect;

light-exposing at least a portion of the hydrophilic light-curable resin solution filled within the flow path(s) using a photomask with an arbitrary pattern;

while leaving the portion cured by light exposure, removing the remaining non-cured portion of the hydrophilic light-curable resin solution from the flow path(s), and then introducing a blocking solution into the flow path(s);

introducing sequentially or simultaneously into the flow path(s) a solution comprising at least an antigen which is a test substance and a labeled secondary antibody or a solution comprising a labeled antigen;

introducing a reagent solution comprising a substrate into the flow path(s) after washing; and detecting the presence of a product of the reaction between the secondary antibody or the antigen and the substrate after a pre-determined time.

The present invention (11) is the method of the present invention (10), wherein the flow path(s) comprises an opening and is 100 μm or more and 5000 μm or less in width and 50 μm or more and 200 μm or less in depth, and wherein a liquid introduced through the opening by capillary effect is allowed to flow down in the direction of the flow path(s).

The present invention (12) is the method of the present invention (10), wherein the flow path(s)
 is a top-open canal formed on a substrate,
 is 100 μm or more and 5000 μm or less in width and 50 μm or more and 200 μm or less in depth, and
 is formed by covering with a cover plate comprising at least an opening.

The present invention (13) is the method of the present invention (10), wherein the flow path(s) comprises an opening and is a space compartmentalized with the inner surface of a capillary, wherein the capillary is in a columnar shape of 50 μm or more and 1000 μm or less, or in a prismatic shape with a side length of 50 μm or more and 1000 μm or less, and wherein a liquid introduced through the opening by capillary effect is allowed to flow down in the direction of the flow path(s).

Herein, "hydrophilic photo-curable resin solution" of the present invention refers to an aqueous liquid composition comprising: (a) a hydrophilic photo-curable resin comprising at least two ethylenic unsaturated bonds in each molecule; and (b) a photopolymerization initiator.

Specifically, the preferably-used hydrophilic photo-curable resin (a) generally has a number average molecular weight within the range of 300 to 30000, preferably 500 to 20000; contains ionic or non-ionic hydrophilic groups sufficient for uniform dispersion in an aqueous medium, such groups including hydroxyl groups, amino groups, carboxyl groups, phosphate groups, sulfonate groups, and ether bonds; and is converted into a water-insoluble resin by curing upon irradiation of active rays having a wavelength within the range of about 250 to about 600 nm. Such usable photo-curable resins include those already known as immobilization carriers for entrapment immobilization (see, for example, Japanese Patent Application Kokoku Publication No. (JP-B) S55-40 (examined, approved Japanese patent application published for opposition); JP-B S55-20676; and JP-B S62-19837).

Representative resins include:

(i) compounds having photo-polymerizable ethylenic unsaturated groups on both ends of polyalkylene glycol, for example, polyethylene glycol di(meth)acrylates resulting from esterification of both end-hydroxyl groups of one mole of polyethylene glycol having a molecular weight of 400 to 6000 with two moles of (meth)acrylic acid;

polypropylene glycol di(meth)acrylates resulting from esterification of both end-hydroxyl groups of one mole of polypropylene glycol having a molecular weight of 200 to 4000 with two moles of (meth)acrylic acid;

urethanated unsaturated polyethylene glycol produced via urethanation of both end-hydroxyl groups of one mole of polyethylene glycol having a molecular weight of 400 to 6000 with two moles of a diisocyanate compound such as tolylene diisocyanate, xylylene diisocyanate, or isophorone diisocyanate, followed by addition of two moles of an unsaturated monohydroxyethyl compound such as 2-hydroxyethyl(meth)acrylate;

urethanated unsaturated polypropylene glycol produced via urethanation of both end-hydroxyl groups of one mole of polypropylene glycol having a molecular weight of 200 to 4000 with two moles of a diisocyanate compound such as tolylene diisocyanate, xylylene diisocyanate, or isophorone diisocyanate, followed by addition of two moles of an unsaturated monohydroxy compound such as 2-hydroxyethyl(meth)acrylate;

(ii) high acid value unsaturated polyester resins: salts of unsaturated polyester having an acid value of 40 to 200 resulting from esterification between a polyhydric alcohol and a polycarboxylic acid component including unsaturated polycarboxylic acid, etc.;

(iii) high acid value unsaturated epoxy resins: unsaturated epoxy resins having an acid value of 40 to 200 resulting from addition of an acid anhydride to hydroxyl groups that remain in a product of addition reaction between an epoxy resin and an unsaturated carboxyl compound such as (meth)acrylic acid, etc.;

(iv) anionic unsaturated acrylic resins: resins resulting from introduction of photo-polymerizable ethylenic unsaturated groups into a copolymer containing carboxyl groups, phosphate groups, and/or sulfonic groups, which is obtained by copolymerization of at least two types of (meth)acrylic monomers selected from (meth)acrylic acids and (meth) acrylic esters, etc.;

(v) unsaturated polyamides: unsaturated polyamides obtained by addition reaction of a water-soluble polyamide such as gelatin with an addition product between a diisocyanate such as tolylene diisocyanate or xylylene diisocyanate and an ethylenic unsaturated hydroxy compound such as 2-hydroxylethyl acrylate, etc.;

(vi) unsaturated polyvinyl alcohol resins: resins with polymerizable unsaturated groups, which are introduced by condensation between N-hydroxyalkyl(meth)acrylamide and a polyvinyl alcohol resin with an average polymerization degree of 300 to 5000 and an average saponification degree of 70% or more. N-hydroxyalkyl(meth)acrylamide includes, for example, N-methylol acrylamide, N-methylol methacrylamide, N,N-dimethylol acrylamide, N,N-dimethylol methacrylamide, N-hydroxyethyl acrylamide, and N-hydroxyethyl methacrylamide.

The above exemplified photo-curable resins may be used individually, or used in combinations of two or more thereof.

Among such photo-curable resins, compounds having photo-polymerizable ethylenic unsaturated groups on both ends of polyalkylene glycol, which are described in (i) above, or such can be used particularly advantageously in the present invention. Representative compounds include resins commercially available from Kansai Paint Co., Ltd. under the following trade names: ENT-1000, ENT-2000, ENT-3400, ENTG-1000, ENTG-2000, ENTG-3800, ENTP-2000, ENTP-4000, ENTV-500, etc.

The photopolymerization initiator (b) is decomposed to generate a radical by light irradiation, which radical serves as a polymerization initiator species for crosslinking reactions between resins having polymerizable unsaturated groups. Such photopolymerization initiators include, for example, α-carbonyls such as benzoin; acyloin ethers such as benzoin ethyl ether; polycyclic aromatic compounds such as naphthol; α-substituted acyloins such as methyl benzoin; and azoamide compounds such as 2-cyano-2-butylazoformamide.

The used proportion of the above components (a) to (b) is not strictly limited. The proportion may be varied within a wide range, depending on the type of each component and such. In general, the proportion preferably used is: 100 parts by mass of component (a), the hydrophilic photo-curable resin, to 0.1 to 5, preferably 0.3 to 3 parts by mass of the photopolymerization initiator (b).

Polystyrene, glass, latex, agarose, and the like can be used for beads onto which a primary antibody is immobilized. Furthermore, magnetic beads, dye-containing beads, fluorescent dye-containing beads, and beads with the surface treated with carboxyl groups, amino groups, epoxy groups, or such can be used. Beads with a diameter of about 0.1 μm to 50 μm can be used.

Peroxidases or other enzymes such as alkaline phosphatases, glucose oxidases, ureases, and the like can be used in the labeling method. Color development, such as fluorescence, chemiluminescence, and coloring, can be achieved by selecting a chromogenic substrate for the enzyme. Alternatively, nano materials such as gold colloids and quantum dots can be used in the labeling method.

EXPLANATIONS OF LETTERS OR NUMERALS

Figure 1:
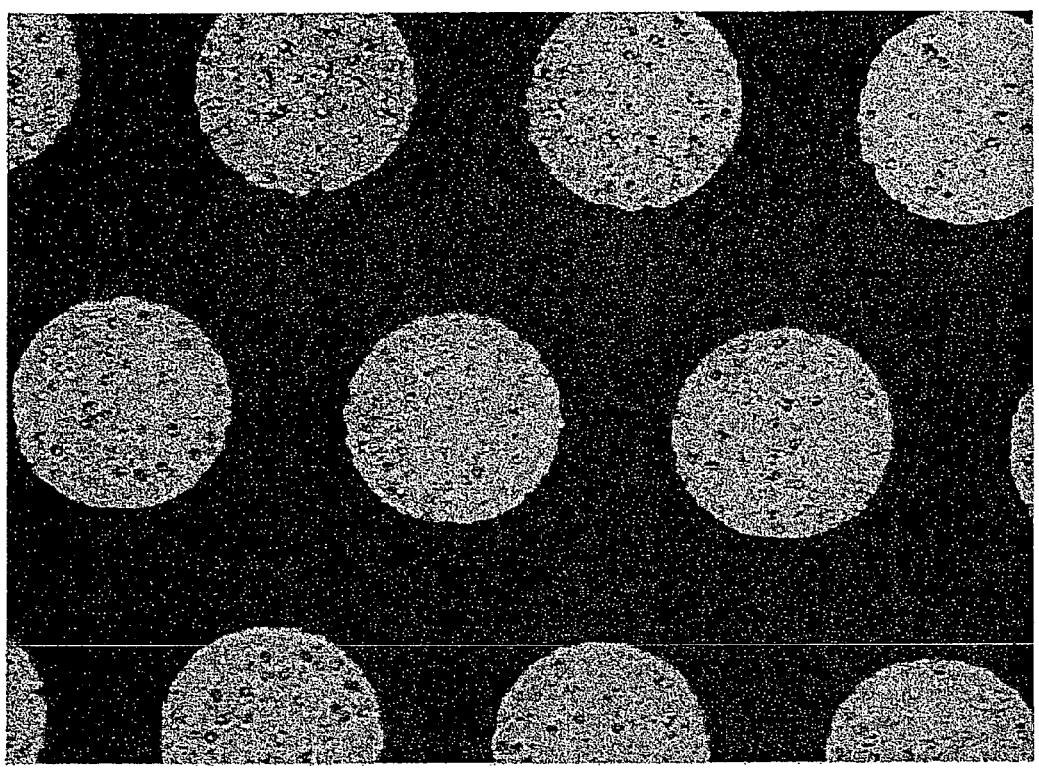
FIG. 1 depicts an example of the photomask used to prepare the microstructures of the present invention (magnified photograph).

C microstructure formed by photo-curing of photo-curable resin
B bead particle having a primary antibody immobilized on its surface
FP flow path portion
1 chip body
2 main flow path
3 sub-flow path
4 sub-flow path
5 column area
6 reservoir tank for washing solution
7 reservoir tank for secondary antibody solution
8 drain tank
9 diaphragm
10 diaphragm
11 sample inlet
12 inlet for sample or such
13 outlet for sample or such
14 detection window
15 capillary tube
16 open end
17 three-dimensional structure

BEST MODE FOR CARRYING OUT THE INVENTION

<Preparation of Photo-Curable Resin Solution>

The photo-curable resin solution used in the present invention was prepared by adding 100 µl of water and 2 µl of the initiator benzoin ethyl ether to 100 µl of an undiluted solution of photo-curable resin (Trade name: ENT-2000; Kansai Paint Co., Ltd.). Herein, water was added for dilution to reduce the viscosity of the solution at the time of introduction into a microchannel and to improve the hydrophilicity of the gel after curing. Applicable dilution ratio is within the range of 0.1 to 1000%.

<Photomask>

The photomask exemplified in FIG. 1 was used in the light exposure treatment of photo-curable resin solutions to prepare three-dimensional structures. The photomask was a film composed of material permeable to exposure wavelength light, and on this photomask, a shade pattern corresponding to non-exposed areas were printed. In the photomask of FIG. 1, circular patterns with a diameter of 400 µm are positioned in the closest arrangement possible at a pitch of 600 µm.

<Microchip Substrate>

Glass substrates were used as the microchip substrates of the present invention. To minimize the substrate cost, a microchip was assembled by bonding a cover plate to a substrate by thermocompression. This cover plate had inlets and outlets produced by boring, and the substrate had top-open linear canals with a flow path width of 1000 µm and a flow path depth of 100 µm. Since reduction of flow path width and/or depth may cause trouble such as clogging when three-dimensional structures are subsequently constructed, and to improve the visibility of color development by reaction products, it is preferable that the flow path width be 100 µm or more and 5000 µm or less, and the depth be 50 µm or more and 200 µm or less. The width and the depth are limited within a range that allows liquids to be introduced by a capillary effect.

After the members described above were prepared, preliminary experiments were conducted by the following procedures, to construct three-dimensional structures of photo-curable resins within the microchannels of the microchips, and to assess various conditions.

(i) A diluted photo-curable resin solution was introduced into a microchip using a pipetter. The solution was allowed to spread over the whole area of the microchannels as it flowed down through the microchannels by the capillary effect. (ii) Then, a photomask was placed on the stage of a fluorescent microscope. The prepared microchip was placed on the photomask such that the photomask is aligned with the microchannels. The irradiation area was set by selecting an object lens and an aperture. Then, the irradiation was performed, the intensity of which was controlled by an ND filter.

Figure 2:
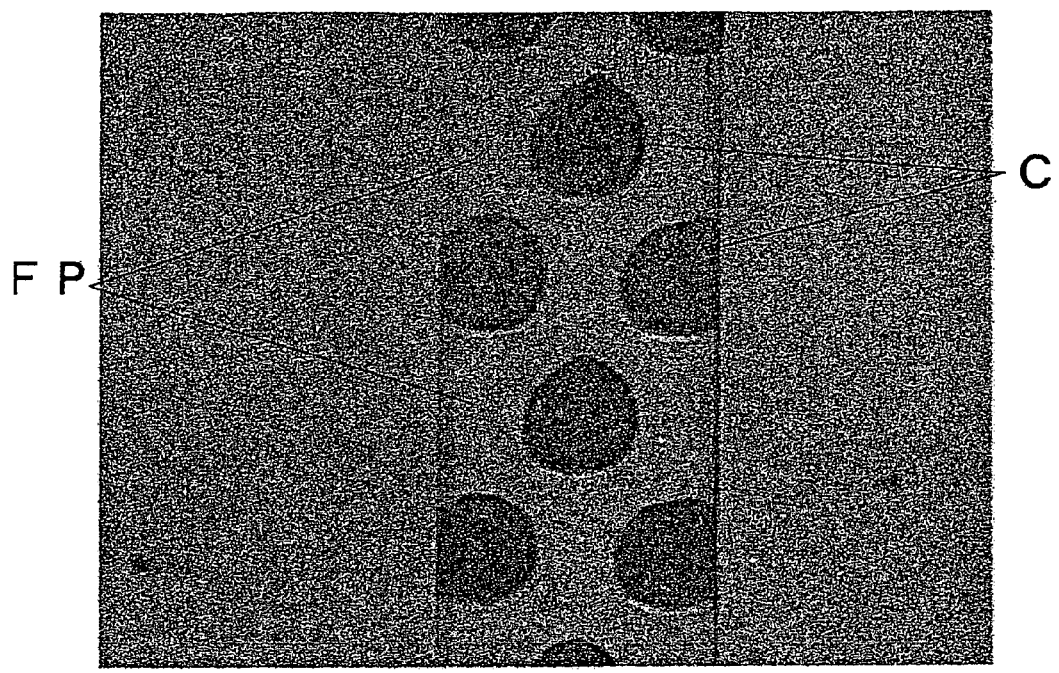
FIG. 2 depicts an example of the arrangement of microstructures in a microchannel of the present invention.

Specifically, recommended conditions are: an irradiation time of three seconds and a light intensity of 13 mW/cm$^2$ at a wavelength of 364 nm, when a 10× object lens is used without any aperture and any ND filter. The result is shown in FIG. 2. "C" in this figure represents the columnar microstructures observed from top, the average diameter of which was estimated to be about 420 µm.

Then, referring to the above conditions of the preliminary experiment, the present inventors constructed similar three-dimensional structures (cylindrical columns in which beads were uniformly dispersed) using a hydrophilic photo-curable resin solution in which primary antibody-bound beads were suspended.

Specifically, (i) a photo-curable resin solution was similarly prepared by mixing 100 µl of ENT-2000, 100 µl of water, and 1 µl of the initiator benzoin ethyl ether. A 100-µl aliquot was taken from a prepared solution of beads on which a primary antibody is immobilized. The aliquot was centrifuged, and then the resulting supernatant was discarded. 100 µl of a photo-curable resin solution was added to the remaining bead solution and mixed.

Next, (ii) 100 µl of the beads-suspended photo-curable resin solution thus prepared was introduced through inlets into microchannels of a prepared microchip, using a pipette. The solution was allowed to spread over the whole microchannel area as it flowed down through the microchannels by the capillary effect.

(iii) Then, a photomask was placed on the stage of a fluorescent microscope. The prepared microchip was placed on the photomask such that the photomask is aligned with the microchannels. The irradiation area was set by selecting an object lens and an aperture. Then, the irradiation was performed, the intensity of which was controlled by an ND filter.

Figure 3:
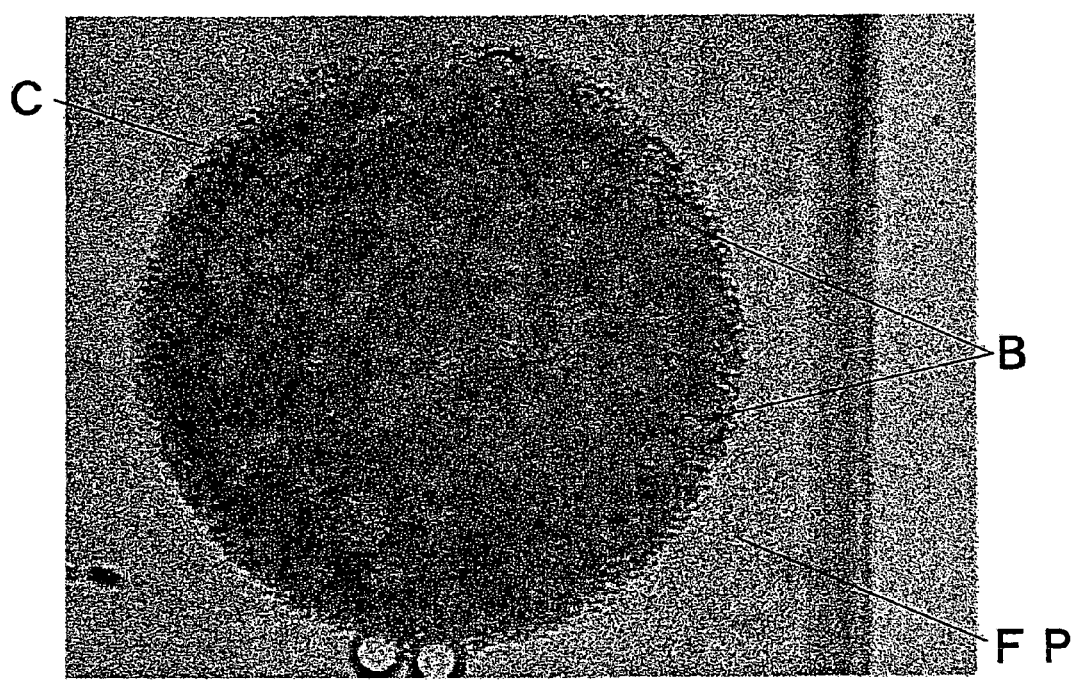
FIG. 3 depicts an example of a microstructure of the present invention, in which beads with an immobilized primary antibody are uniformly dispersed in a hydrophilic photo-curable resin (magnified photograph).

Next, leaving the portions cured by light exposure, the non-cured portions of the photo-curable resin solution were washed off the microchannels. Thus, as shown in FIG. 3, the columnar structures of photo-curable resins in which beads were almost uniformly dispersed could be constructed in the microchannels (the average diameter of the columnar structures was estimated to be 420 μm). The dim particles ("B" in the figure) within the columnar structure show the silhouettes of beads dispersed in cured resin. In FIG. 3, a grey area ("FP") surrounds the column in which beads are uniformly dispersed. This indicates that the periphery around the column developed a pale blue color due to coloring of the chromogenic substrate, resulting from the enzymatic reaction.

When water was introduced into the microchannels using a syringe, the columnar structures did not break up. The three-dimensional columnar structures still remained intact even when the aqueous solution introduced into the microchip was removed using a centrifuge. In view of the above, the three-dimensional structures thus constructed were confirmed to have a physical strength sufficient for usually-envisaged microchip manipulations. Thus, it was demonstrated that solutions can be introduced into microchannels using capillary effects, and can be rapidly drained out by treatments using a centrifuge or such.

Figure 4:
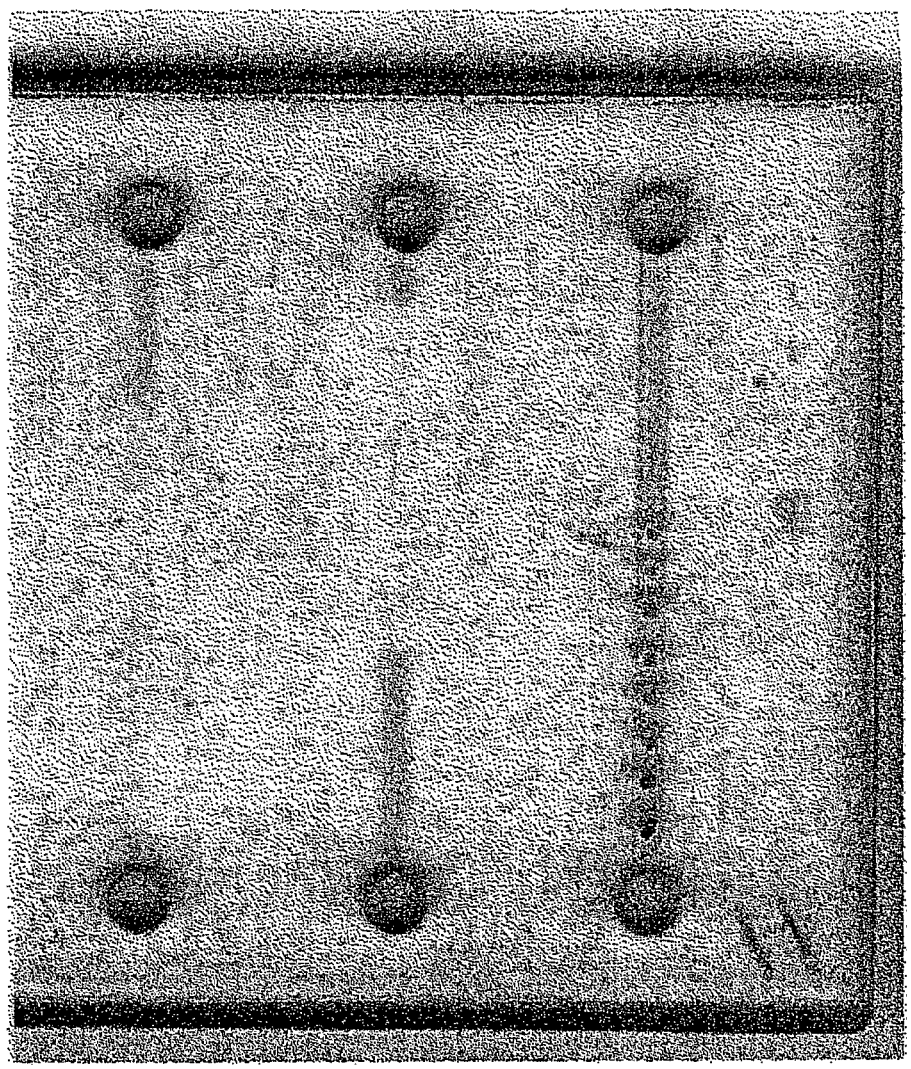
FIG. 4 depicts an example of a microchannel of the present invention, in which microstructures with different bead colors are arranged in the direction of flow path.

Furthermore, an assay that enables simultaneous detection of different types of analytes was constructed within a single microchannel by repeating light exposure treatment while varying the type of beads (the type of antibody immobilized on the surface) introduced. The assay is shown in FIG. 4. Here, the color of the beads introduced into each column was also varied in correspondence with the type of antibody, taking into consideration the visibility at the time of detection (in the figure, different tones indicate different column colors). Furthermore, it is also possible to change column color tones or gradations along the microchannel direction by varying the mixing ratio of colored beads to white or transparent beads.

Meanwhile, by applying the technique of using colored columns made by selecting bead color, it is possible to improve the sensitivity of visual detection. It is difficult to visually detect color development unless the concentration of a sample is very high, due in part to individual differences. Thus, visual color detection has practical limitations in general use. For example, the sensitivity of ordinary individuals to blue color development is estimated to be equivalent to an output value of a thermal lens microscope of about 1000 μV, when the depth is 100 μm.

However, detection of color development in samples with a coloring intensity of the above level requires much skill. In addition, most types of analytes with high needs to be tested in general use usually have concentrations corresponding to less than 1000 μV. Thus, if the sensitivity of visual detection can not be improved, it could impair practical use of color detection.

In view of the above, the present inventors focused on differences in visibility caused by complementary colors, and devised a microchannel arrangement including five groups of columns, having, for example, the following arrangement: a bead column group of a color that is opposite on the color wheel to the blue of SAT Blue (orange) was positioned in the center; bead column groups of yellow-green and violet that are at 90-degree angles on the color wheel were placed before and after the orange group; and two blue bead column groups were arranged before and after the yellow-green and violet groups.

This arrangement facilitates detection of at least the color development in the orange column group in the center, even in a sample in which the blue color development is weak due to a low analyte concentration (for example, a sample with a concentration corresponding to a thermal lens microscope output value of slightly below 1000 μV). In some cases, to make visual observation easy, the cover plate over the microchannel area where columns are arranged may be convexed to a desired curvature to enable a magnified view.

Meanwhile, the immunoassay chips of the present invention succeeded in considerably shortening the time required for assay to about 20 minutes, as compared to the time required for the conventional titer plate method (4 to 5 hours for the heart disease marker BNP). Although this was considered to be comparable to an assay time of about 15 minutes for the so-called microchip ELISA method exemplified in Patent Document 1 listed above, the present inventors further improved the column design.

Specifically, the immunoassay microchips of the present invention shown in FIG. 3 have been designed such that beads are uniformly dispersed throughout the columns. This system takes time because the coloring agent is introduced into the columns only after the analyte impregnates the whole column, and time is inevitably required for the coloring agent to impregnate all the columns, and for the colored reaction products to penetrate out from the columns to uniformly diffuse in the flow path around to the columns.

Consequently, the present inventors first limited the bead distribution to as surrounding the columnar three-dimensional structures to shorten the time required for the impregnation. Specifically, the inventors succeeded in shortening the time required for the impregnation by preparing cylindrical columns as described below: first a hydrophilic photo-curable resin layer that serves as a support was formed; a hydrophilic photo-curable resin solution containing a suspension of beads having a primary antibody immobilized on their surface was introduced; and then, light exposure treatment was applied coaxially with the axis of the support.

In this case, the amount of reaction products is reduced with the decrease in bead amount. Thus, it is preferable to omit the process of reaction product penetration to the flow path surrounding the columns, and locally and directly analyze the surfaces with beads distributed in a doughnut-like shape on each column by a thermal lens microscope or the like. This enables further shortening of the time required for analysis, by about five to ten minutes in total.

Figure 6:
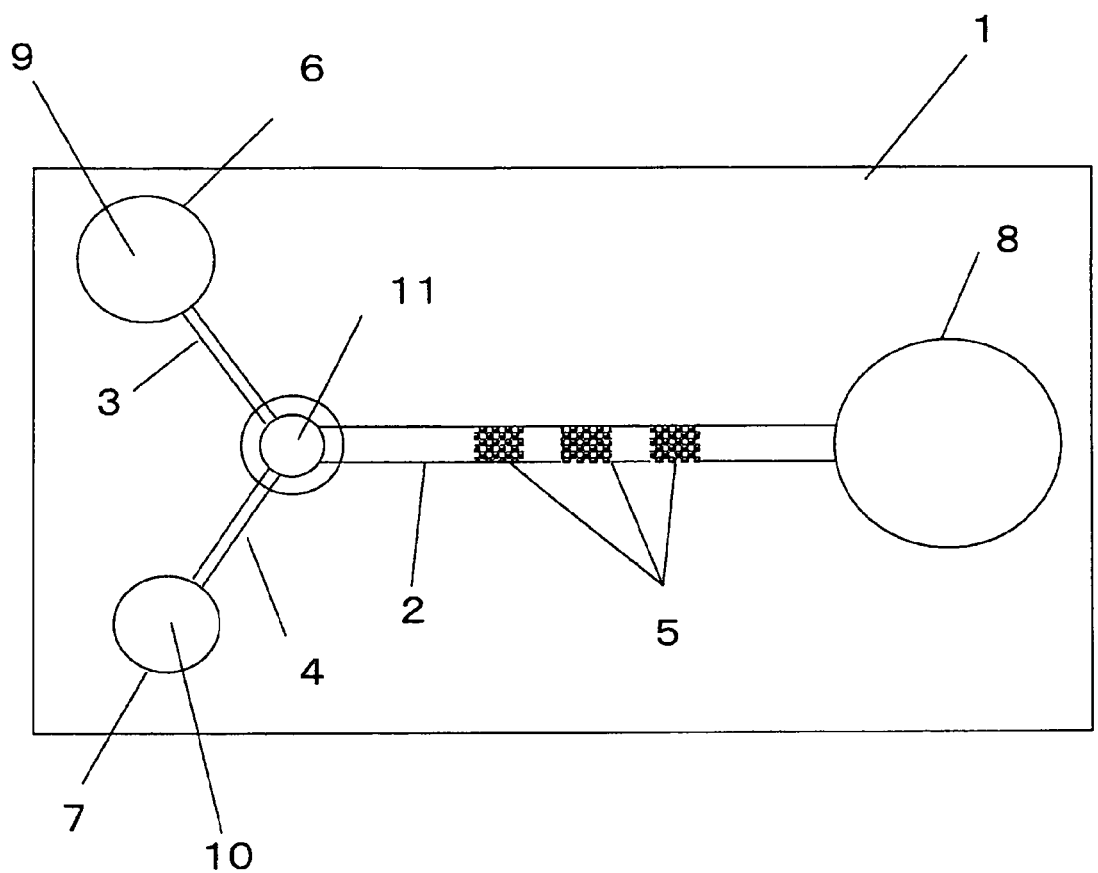
FIG. 6 is a schematic diagram showing an example of the layout of a microchip of the present invention.

An example of the layout of an immunoassay microchip of the present invention is schematically illustrated in FIG. 6. The chip body (1) consists of a glass substrate and a cover plate. Canals for the main flow path (2) and sub-flow paths (3 and 4), as well as concaves for a reservoir tank for the washing solution (6) and a reservoir tank for secondary-antibody solution (7), have been formed on the glass substrate.

Several column areas (5) are arranged in the main flow path (2). In these column areas, a grove of cylindrical columns (microstructures of photo-curable resins in which beads are uniformly distributed) stand in the direction of the depth of the canal. Gaps are left between the flow path walls and the columns so as not to interrupt the liquid flow. Each column area (5) is made using cylindrical columns containing uniformly distributed beads of a different color and/or uniformly distributed beads on which a different type of primary antibody is immobilized. This enables simultaneous analysis of different analytes in different areas and/or simultaneous analysis using different visibilities in different areas.

Furthermore, one end of the main flow path (2) is connected to a sample inlet (11) formed on the cover plate as well as the corresponding concave, while the other end is connected to a drain tank (8). The concave corresponding to the sample inlet (11) is connected to the two sub-flow paths (3 and 4). The other sides of the sub-flow paths (3 and 4) are connected to the reservoir tank for the washing solution (6) and the reservoir tank for the secondary antibody solution (7), respectively.

A sample containing an analyte(s) is introduced into the sample inlet (11) using a microsyringe or a pipette. The main flow path (2) is significantly wider than the sub-flow paths (3 and 4). Thus, the introduced sample does not flow into the sub-flow paths (3 and 4), but instead, streams into the main flow path (2) due to the capillary effect. After completion of the introduction of the sample into the main flow path (2), the sample inlet (11) is closed with a stopper or such.

Diaphragms composed of an airtight elastic body (9 and 10) are placed in the cover plate areas over the reservoir tank for the washing solution (6) and the reservoir tank for the secondary antibody solution (7). When a washing solution or a secondary antibody solution containing a secondary antibody needs to be introduced into the main flow path (2), the liquid in the reservoir tanks (6 and 7) is made to flow out by pushing down the corresponding diaphragms (9 and 10). Since the sample inlet (11) is tightly closed as described above, the positions of the washing solution and the secondary antibody solution within the main flow path (2) can be controlled by adjusting the pressing strength of the diaphragms (9 and 10).

Figure 7:
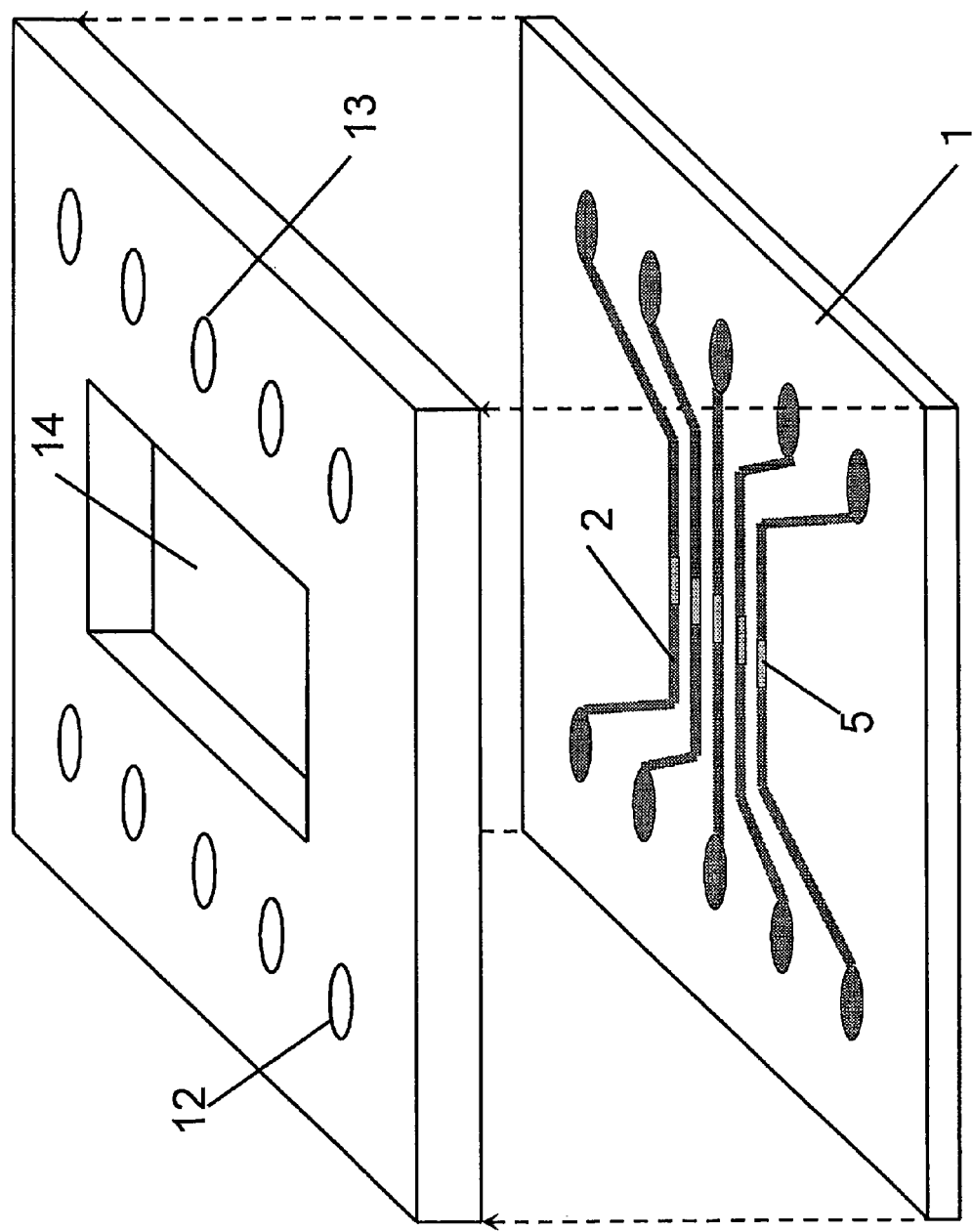
FIG. 7 is a schematic diagram showing an example of a microchip of the present invention, in which multiple flow paths are arranged.

Meanwhile, at least the portions of the cover plate over the column areas (5) are designed to be transparent. Thus, the colors and such developed by introduced solutions at these areas can be observed from outside. FIG. 6 illustrates an embodiment in which a single main flow path (2) is produced on a single microchip to provide a testing kit with a reservoir tank and a drain tank premade within the chip. On the other hand, as shown in FIG. 7, when a microchip is designed envisaging manual introduction and draining of reagents and washing solutions using a pipette or such, similar to introduction and draining of analytes, several main flow paths (2) comprising column areas (5) may be arranged on a microchip body (1), on which main flow path inlets for samples or such (12) and outlets for samples or such (13) are independently created. Such microchips are preferred, since they allow various immunoassays to be carried out simultaneously. As seen in FIG. 7, the external size of a microchip can be reduced compared to the exemplary arrangement shown in FIG. 5, or the like, when column areas (5) are concentrated below the detection window (14) consisting of a cover glass. Since this improves the operability and such in positioning in relation to detection systems such as microscopes, such chips are more preferred.

The immunoassay microchips of the present invention are designed such that the volume of the flow path portion around each column is reduced to a range that does not interfere with manipulations. Thus, the color development reaches a constant level as a result of the rate-limiting transfer of substrates to reaction products in about ten minutes after introduction of a secondary antibody solution, even without introducing any reagent to stop the redox reaction of the substrates. As a result, the assay becomes less time-dependent and thus the assay results are not strongly influenced by the analysts' skills and such.

EXAMPLES

Example 1

Illustrated below is an example of the application of a microchip of the present invention to the detection of human brain natriuretic peptide (BNP), a cardiac disease marker. The primary antibody immobilized on beads, the antigen, and the enzyme-labeled secondary antibody used were BC203, BNP, Fab'-HRP, respectively, which were provided by Shionogi & Co., Ltd.

The procedure was as follows: a mixed solution prepared by combining primary antibody-immobilized beads with a photo-curable resin solution (100 µl of ENTG-2000, 100 µl of water, and 1 µl of the initiator benzoin ethyl ether) was introduced into microchannels by the capillary effect. Then, light exposure with an irradiation time of four seconds was performed using a photomask and a 4× object lens without any ND filter.

The non-cured photo-curable resin solution was removed from the microchannels. Then, bead columns in the microchannels were treated with 2 µl of a blocking solution containing 1% bovine serum albumin (BSA) and phosphate-buffered saline (PBS) to prevent non-specific binding of proteins to beads or such. The time required for this blocking treatment is about 60 minutes.

Next, 2 µl of a solution containing the above antigen (used as an analyte) and the secondary antibody was introduced into the microchannels. The solution was allowed to stay for ten minutes, considering the time required for the reaction with the primary antibody immobilized on beads. Then, the microchannels were washed with 10 µl of a mixed solution of 0.01% polyoxy monolaurate Tween20 and PBS.

Figure 5:
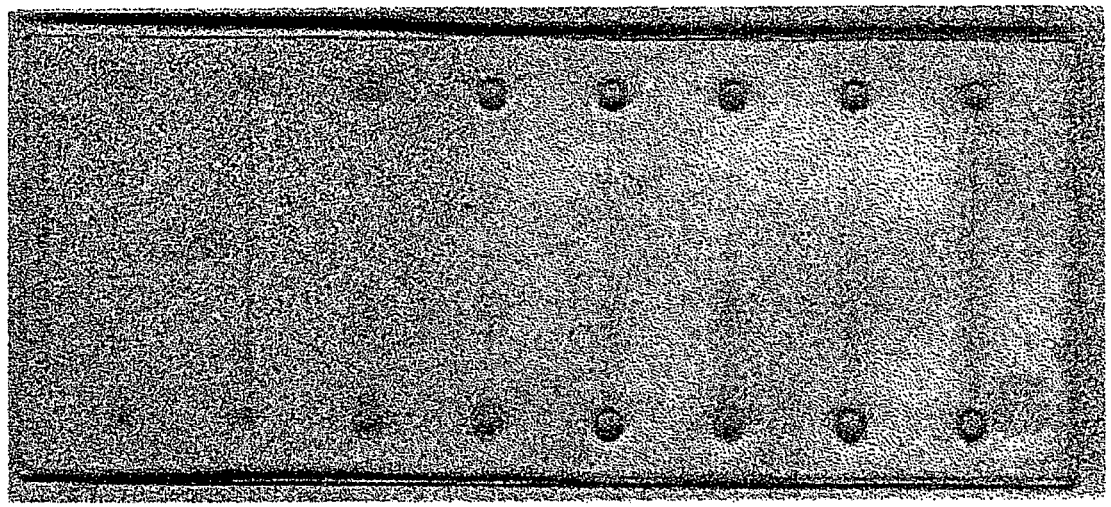
FIG. 5 depicts an example of the color development in a microchip of the present invention.

After the above, 2 µl of SAT Blue, a chromogenic redox reagent, was introduced, and then contacted with the detection system of primary antibody immobilized on beads/antigen/enzyme-labeled secondary antibody. Blue color was developed via a redox reaction by the enzyme label. The result is shown in FIG. 5. In FIG. 5, the flow paths are colored blue in their full width in the dark-banded zones along the microchannels in which bead columns are arranged.

Figure 8:
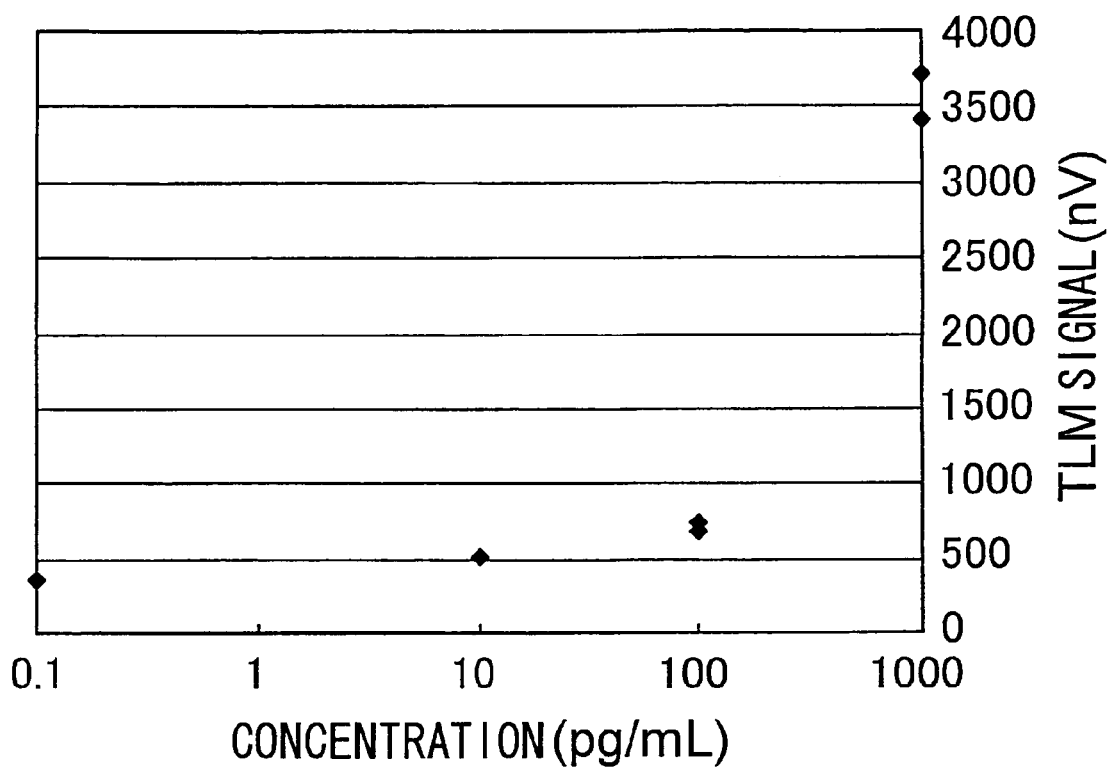
FIG. 8 depicts an example of the concentration standard curve for BNP, a cardiac disease marker, according to Example 1 of the present invention.

The reagent reacted with the enzyme, which penetrated out from the columnar structures to the surrounding flow path portions and developed a blue color in the flow path portions, was detected using a thermal lens microscope. The treatments as described above were repeated while varying the concentration of the introduced antigen within the range of 0.1 to 1000 pg/ml. The result is illustrated in FIG. 8 using a standard curve format, in which the vertical axis indicates the output signal intensity of the thermal lens microscope.

As a result, the reproducibility was high, and the detection limit was estimated to be about 10 pg/ml. A cut-off level of 100 pg/ml is set in heart failure diagnosis, and thus, the detection limit in the present example was assessed to be sufficient for practical use.

Example 2

An example of the application of the present invention to the detection of prion proteins is illustrated below.

The conditions used were the same as those described in Example 1 above, except that the primary antibody, the antigen, and the enzyme-labeled secondary antibody used in the detection system were T2, rPrP, and T17, respectively.

Figure 9:
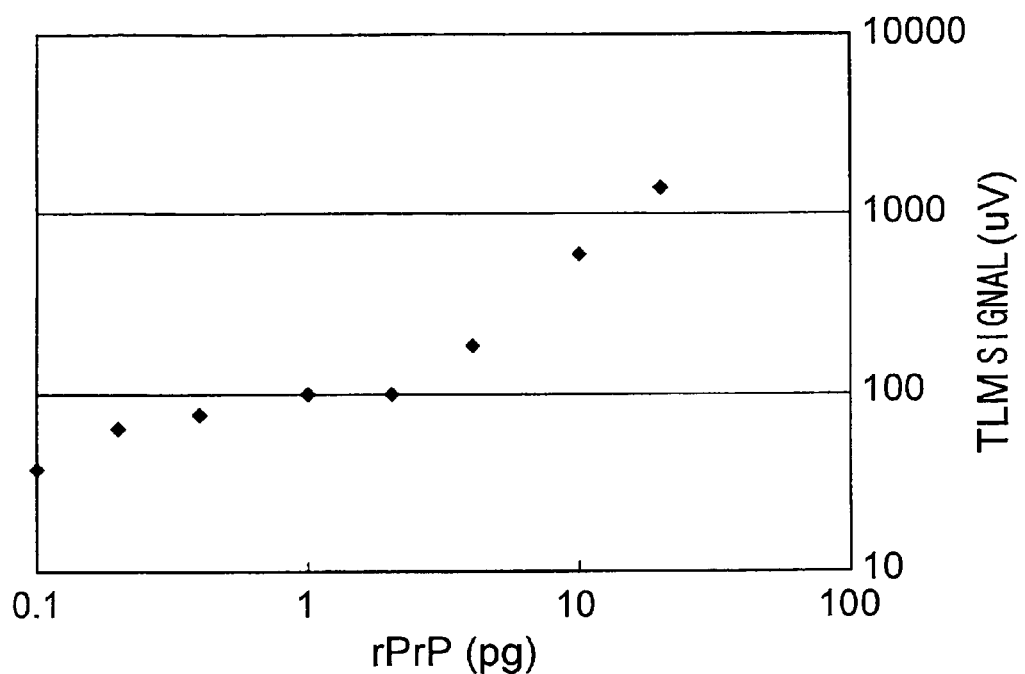
FIG. 9 depicts an example of the concentration standard curve for rPrP, a prion protein, according to Example 2 of the present invention.

The result is shown in FIG. 9. The detection limit was estimated to be about 4 pg per measurement. This detection limit is comparable to that of the ELISA method, which is estimated to be 60 pg. The detection time of the present invention is only about 20 minutes, while that of the ELISA method is about four to five hours. Thus, the present invention was assessed to have a sufficient advantage for practical use.

Example 3

The present inventors also aimed to prepare immunoassay microchips by constructing the microstructures of the present invention in preexisting or prepared capillary tubes (capillaries that enable introduction of liquids by the capillary effect), in which preexisting inner spaces of the tubes were used as flow paths, instead of using flow paths formed on a substrate by the conventional lithography technique.

The cross-section of a capillary tube may be circular or polygonal. When the cross-section is circular, the diameter may be within the range of 50 to 1000 μm. Alternatively, when the cross-section is polygonal, the length of a side may be within the range of 50 to 1000 μm. The material of the tubes is not particularly limited; glass tubes and plastic tubes can be used.

However, the material needs to have transparency to light exposure wavelengths, to the extent required for light exposure, since patterning of microstructures is required to use capillary tubes as flow paths in which the microstructures of the present invention are constructed. Furthermore, use of capillary tubes with cross-sections that are exceedingly complicated in shape should be avoided from the viewpoint of the patterning accuracy of microstructures.

Figure 10:
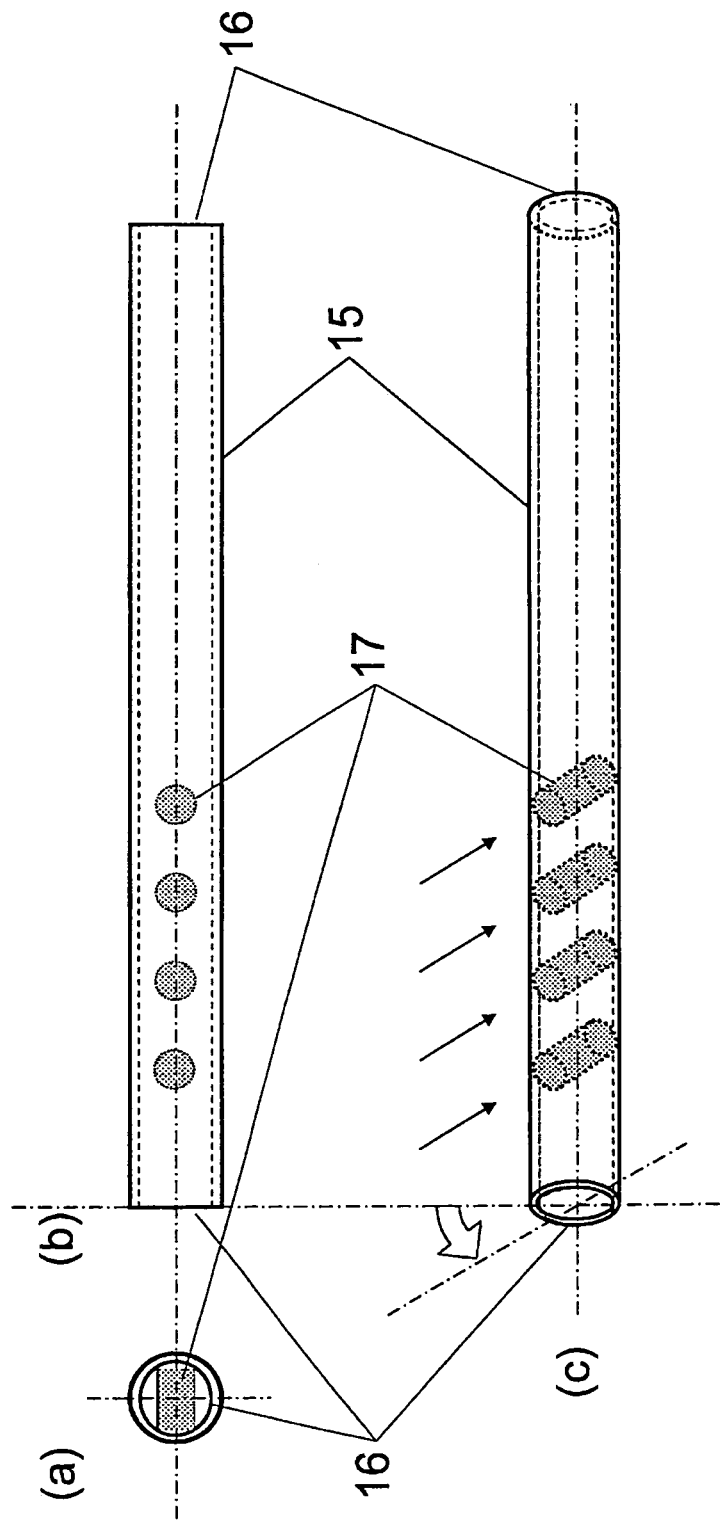
FIG. 10 is a schematic diagram showing an example of a microchip of the present invention, in which three-dimensional microstructures are arranged in a capillary tube, according to Example 3 of the present invention.

An example of the arrangement of microstructures using a cylindrical capillary tube is schematically illustrated in FIG. 10. FIG. 10(a) is a lateral view of the capillary tube as viewed from the side of one open end. FIG. 10(b) is a front view of the capillary tube as viewed from the direction of the axis of light to which the microstructures formed within the tube are exposed. FIG. 10(c) is a perspective view of the capillary tube.

The capillary tube (15) used has open ends (16) on both sides. The inner diameter is 630 μm (the outer diameter is 900 μm); the axis length is 32 mm; and the inner volume is 10 μl. FIG. 10 is only a schematic illustration, and thus does not show the exact dimensional ratios and such.

Specifically, the microstructures of the present invention were constructed in a capillary tube by the procedure described below, using a mouse anti-human IgE monoclonal antibody (Beckman Coulter, Inc.) as the primary antibody, human IgE (Yamasa Corporation) as the antigen, and an HRP-anti-human IgE antibody (Goat-Poly; KPL, Inc.) as the enzyme-labeled secondary antibody.

Figure 11:
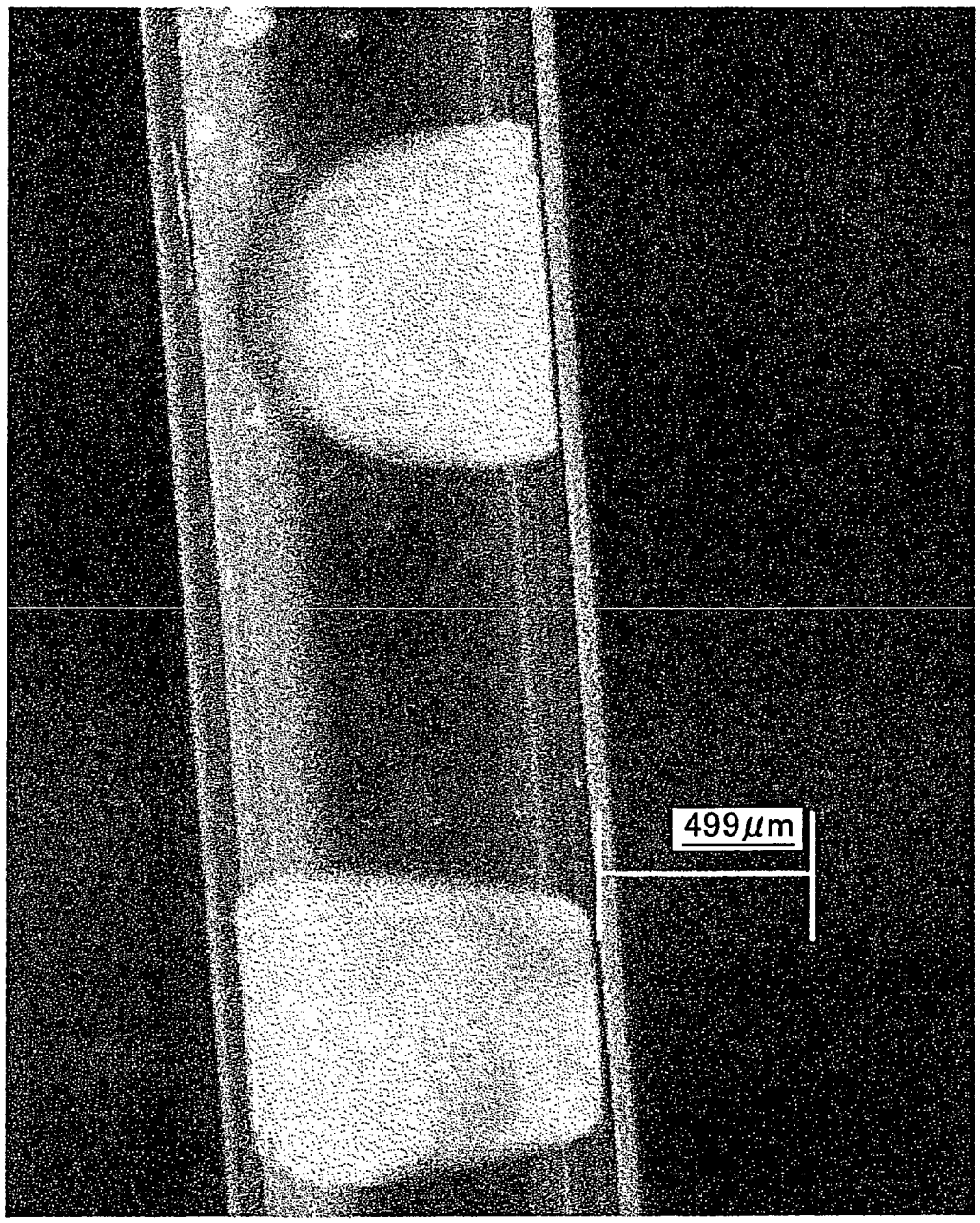
FIG. 11 is a micrograph of the microchip according to Example 3 of the present invention.

Either end of a capillary tube was immersed in a liquid, in which primary antibody-immobilized beads were mixed and suspended in a photo-curable resin solution. After the photo-curable resin solution was introduced into the capillary tube by the capillary effect, a photomask was placed at a position outside the tube, which corresponds to the position at which the microstructures were to be arranged. The photo-curable resins in the predetermined areas were cured by irradiating light for three seconds, the intensity of which was adjusted to 55 mW/cm$^2$, using an optical system with a 4× object lens without any filter. The non-cured portions of the photo-curable resin solution in the areas shaded by the photomask were removed by draining The photo-cured resins remain as microstructures (17) lying across the flow path in the capillary tube (15) in the areas exposed to the light. FIG. 11 is a micrograph showing the arrangement. As shown in FIG. 11, three-dimensional structures (17) having a cross-section in accordance with the photomask pattern remain within the capillary tube (15). The depth of curing of photo-curable resins may be altered by controlling the irradiation intensity of an exposure light source and exposure time. Thus, columnar shapes or prismatic shapes do not necessarily reach the opposite side of the capillary tube in accordance with the photomask pattern, due in part to the refraction effect produced by the shape of the capillary tube. Three-dimensional structures with a bubble-like shape adhering to the inner surface of the tube can also be constructed (the white area on the left side of FIG. 10). Selection of such a shape for the three-dimensional structures has the advantages of reduced flow path resistance, and easy introduction and draining of liquids such as reagents and analytes.

10 μl of a blocking solution containing 1% bovine serum albumin (BSA) and phosphate-buffered saline (PBS) was introduced into the capillary tube including the three-dimensional structures. The solution was allowed to stay for 60 minutes. After this blocking treatment, 10 μl of a solution containing the above antigen (human IgE (Yamasa Corporation)) and the secondary antibody (an HRP-anti-human IgE antibody (Goat-Poly; KPL, Inc.)) was similarly introduced by the capillary effect. The solution was allowed to stay for ten minutes. Then, the capillary was washed with 10 μl of a mixed solution containing 0.01% polyoxy monolaurate Tween20 and PBS. 10 μl of SAT Blue, a chromogenic redox reagent, was introduced and allowed to stay for ten minutes. As a result, blue color development was confirmed by visual observation.

Example 4

Orange beads and white beads on which the same primary antibody as that described in Example 3 was immobilized were prepared separately and used to construct three-dimensional structures within different capillary tubes by a method similar to that described in Example 3. 10 μl of a blocking solution containing 1% bovine serum albumin (BSA) and phosphate-buffered saline (PBS) was introduced into the capillary tubes. The solution was allowed to stay for 60 minutes. After this blocking treatment, 10 μl of a solution containing the above antigen (human IgE (Yamasa Corporation)) and the secondary antibody (an HRP-anti-human IgE antibody (Goat-Poly; KPL, Inc.)) was similarly introduced by the capillary effect. The solution was allowed to stay for ten minutes. Then, the capillary was washed with 10 μl of a mixed solution containing 0.01% polyoxy monolaurate Tween20 and PBS. 10 μl of SAT Blue, a chromogenic redox reagent, was introduced and allowed to stay for ten minutes.

As a result, it was confirmed that the visibility of the color developed in the capillary tube to which the orange beads were introduced was superior to that of the color developed in the capillary tube to which the white beads were introduced, probably because of the stronger contrast between the color of the beads and the color of the reagent, while the intensity of the color developed in the capillary tube introduced with white beads is identical in terms of physical quantity to that of the color developed in the capillary tube introduced with orange beads.

INDUSTRIAL APPLICABILITY

The present invention provides immunoassay microchips and immunoassay kits that enable rapid, simple, and highly-sensitive detection, even when the analyte amount is small, by subsequently constructing three-dimensional structures of bead columns in general-purpose microchannels on a substrate (and in conventional capillary tubes). The present invention also provides immunoassay methods using the microchips.

The present invention also provides highly portable immunoassay microchips and immunoassay kits that enable quantitative analysis of samples in trace amounts by assaying the reaction products in columns using analytical devices such as a thermal lens microscope. The present invention further enables not only simultaneous detection of multiple types of analytes, but also visual detection of analytes in a low concentration range without any specific analytical device, except in extremely low concentrations, due to the improvement in visibility achieved by use of colored beads. Furthermore, the present invention can reduce the possibility of exposure to radioisotopes, toxic substances, and materials suspected to be infectious, which have been avoided from a practical viewpoint.

The invention claimed is:

1. An immunoassay microchip, comprising a microchannel(s) comprising a flow path(s) with a microstructure(s) having a three dimensional structure,
    wherein the microstructure(s) retains microbeads uniformly dispersed in a photo-cured hydrophilic resin in all directions of the three dimensional structure;
    wherein the microbeads have a primary antibody immobilized on their surface; and
    wherein the microstructure(s) is patterned into an arbitrary shape by light exposure treatment of the hydrophilic light-curable resin solution in which the microbeads are suspended;
    wherein the microstructure(s) has an external diameter of about 40 μm (in width) and a height of 100 μm (in depth); and
    wherein a cross-section of the microchannel is divided into a flow path portion and a microstructure portion retaining uniformly-dispersed beads so that the flow path portion in the microchannel is secured between the microstructures without large increase in flow path resistance.

2. The immunoassay microchip of claim 1, wherein microstructure(s) retaining uniformly dispersed microbeads that have a primary antibody immobilized on their surface and have different color tones are sequentially arranged along the flow path(s).

3. The immunoassay microchip of claim 1, wherein the flow path(s) is formed by a canal formed on a substrate and a cover plate that comprises at least an opening.

4. The immunoassay microchip of claim 3, wherein the flow path(s) is 100 μm or more and 5000 μm or less in width and 50 μm or more and 200 μm or less in depth, and wherein at least a portion of the flow path(s) comprises a region with a flow path cross-sectional area that enables a liquid introduced by a capillarity to flow down in the direction of the flow path(s).

5. The immunoassay microchip of claim 1, wherein the flow path(s) is a space compartmentalized with the inner surface of a capillary comprising at least an opening.

6. The immunoassay microchip of claim 5, wherein the flow path(s) is in a columnar shape with a diameter of 50 μm or more and 1000 μm or less, or in a prismatic shape with a side length of 50 μm or more and 1000 μm or less, and wherein the flow path(s) is a space compartmentalized with the inner surface of a capillary comprising at least an opening.

7. A kit for immunoassay, wherein the immunoassay microchip of any one of claims 1 or 2 to 6 is packed together with a solution comprising a labeled secondary antibody or a solution comprising a labeled antigen, a washing solution, and a reagent solution comprising a substrate, such that the solutions can be introduced into a flow path of the microchip.

* * * * *